US011911193B2

(12) United States Patent
Nowak

(10) Patent No.: US 11,911,193 B2
(45) Date of Patent: Feb. 27, 2024

(54) METHOD AND APPARATUS FOR GENERATING A RESULTANT IMAGE DATASET OF A PATIENT

(71) Applicant: Siemens Healthcare GmbH, Erlangen (DE)

(72) Inventor: Tristan Nowak, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/057,831

(22) Filed: Nov. 22, 2022

(65) Prior Publication Data
US 2023/0165543 A1 Jun. 1, 2023

(30) Foreign Application Priority Data

Nov. 29, 2021 (DE) ...................... 10 2021 213 439.4

(51) Int. Cl.
*A61B 6/03* (2006.01)
*A61B 6/00* (2006.01)

(52) U.S. Cl.
CPC ............ *A61B 6/032* (2013.01); *A61B 6/4208* (2013.01); *A61B 6/481* (2013.01); *A61B 6/482* (2013.01); *A61B 6/5258* (2013.01)

(58) Field of Classification Search
CPC ....... A61B 6/032; A61B 6/4208; A61B 6/481; A61B 6/482; A61B 6/5258
See application file for complete search history.

(56) References Cited

U.S. PATENT DOCUMENTS

| | | | |
|---|---|---|---|
| 2010/0166277 | A1 | 7/2010 | Raupach |
| 2010/0220912 | A1 | 9/2010 | Bruder et al. |
| 2012/0207270 | A1 | 8/2012 | Flohr et al. |
| 2016/0262713 | A1 | 9/2016 | Flohr et al. |
| 2017/0086769 | A1 | 3/2017 | Allmendinger et al. |
| 2017/0301082 | A1 | 10/2017 | Allmendinger et al. |
| 2019/0212278 | A1* | 7/2019 | St-Aubin ............. G01N 23/087 |

FOREIGN PATENT DOCUMENTS

| | | |
|---|---|---|
| DE | 102008063311 A1 | 7/2010 |
| DE | 102009010501 A1 | 9/2010 |
| DE | 102011004120 A1 | 8/2012 |
| DE | 102015204450 A1 | 9/2016 |
| DE | 102015218928 A1 | 3/2017 |
| DE | 102016221684 A1 | 6/2017 |
| DE | 102019210355 A1 | 1/2021 |

OTHER PUBLICATIONS

Mannil, Manoj, et al. Modified dual-energy algorithm for calcified plaque removal: evaluation in carotid computed tomography angiography and comparison with digital subtraction angiography. Investigative Radiology, 2017, 52. Jg., Nr. 11, S. 680-685.*.

(Continued)

*Primary Examiner* — Courtney D Thomas
(74) *Attorney, Agent, or Firm* — Harness, Dickey & Pierce, P.L.C.

(57) ABSTRACT

One or more example embodiments of the present invention relates to a method for generating a resultant image dataset of a patient based on spatial distributions of materials in the patient.

20 Claims, 3 Drawing Sheets

(56) References Cited

OTHER PUBLICATIONS

He, Kaiming et al.: "Guided Image Filtering"; IEEE Transactions on Pattern Analysis and Machine Intelligence; vol. 35; No. 6; pp. 1397-1409; 2013.
Leng, Shuai et al.: "Noise reduction in spectral CT: Reducing dose and breaking the trade-off between image noise and energy bin selection"; Medical Physics; vol. 38; No. 9; pp. 4946-4957; 2011; doi: 10.1118/1.3609097.
Maaß et al."Image-based dual energy CT using optimized precorrection functions: A practical new approach of material decomposition in image domain.", Med. Phys. 2009, 36. Jg. Nr. 8, S. 3818-3829.
Le et al.: "Least squares parameter estimation methods for material decomposition with energy discriminating detectors", Med. Phys. 2011, 38. Jg., Nr. 1., S. 245-255.
Kalender, W. et al: "Materialselektive Bildgebung und Dichtemessung mit der Zwei-Spektren-Methode 1. Grundlagen und Methodik"; In: Digitale Bilddiagnostik; vol. 7, Year: 1987, H. 2, pp. 66-72; Georg Thieme Verlag.
Lu et al.: "A learning-based material decomposition pipeline for multi energy x-rayy-imaging", Med.Phys., 2019, 46 Jg., Nr. 2, S 689-703.
German Office Action and English translation thereof dated Aug. 10, 2022.
German Decision to Grant and English translation thereof dated Nov. 25, 2022.

* cited by examiner

METHOD AND APPARATUS FOR GENERATING A RESULTANT IMAGE DATASET OF A PATIENT

CROSS-REFERENCE TO RELATED APPLICATION(S)

The present application claims priority under 35 U.S.C. § 119 to German Patent Application No. 10 2021 213 439.4, filed Nov. 29, 2021, the entire contents of which are incorporated herein by reference.

FIELD

One or more example embodiments of the present invention relates to a method and an apparatus for generating a resultant image dataset of a patient, an imaging device comprising an apparatus for generating a resultant image dataset, as well as an associated computer program product and a computer-readable storage medium.

STATE OF THE ART

With the aid of modern imaging methods, two or three-dimensional image data is often generated which can be used for visualizing a mapped examination object and additionally for other uses. The imaging methods are often based upon the capture of X-ray radiation wherein so-called projection scan data is generated. For example, projection scan data can be acquired with the aid of a computed tomography (CT) device. In CT systems, a combination of an X-ray source and, mounted opposite thereto, an X-ray detector, said combination being arranged on a rotating gantry, typically revolves about a scanning space in which the examination object (which is identified below as a patient, but without restricting the generality) is situated. The center of rotation (also known as "isocenter") therein coincides with a so-called system axis, also known as the z-axis, which extends in the z-direction. During one or more rotations, the patient is irradiated with X-ray radiation from the X-ray source, wherein with the aid of the X-ray detector positioned opposite thereto, image datasets in the form of projection scan data or X-ray projection data are captured. On the basis of the projection scan data, via a suitable reconstruction algorithm, image datasets for a spatial representation of the patient can be generated in the image space. A reconstruction and/or a reconstruction algorithm involves any desired image reconstruction algorithm as known in the art, for example, a weighted filtered back projection (WFBP), as is often used in computed tomography. Alternative reconstruction algorithms are equally possible and their application belongs within the capability of a person skilled in the art.

In computed tomography and also in other radiographic processes, for example, by way of the use of different tube voltages or the use of an energy-resolving detector, a plurality of images of the same object volume can be reconstructed which differ in the X-ray attenuation caused by the material present by reason of the different X-ray spectra, i.e. the X-ray quantum energy distribution, recorded by the detector. On the basis thereof, for example, an identification of at least two materials can then be carried out via a material breakdown.

If at least two different X-ray quantum energy distributions are available, it is possible, for example, when recording with an iodine-containing contrast medium, to carry out a breakdown of the spectral input volume into a calcium volume and an iodine volume. Thereafter, given a suitable selection of the material parameters, in the iodine volume, the attenuation caused by the calcium is removed for example in order, on the basis thereof, to enable an improved evaluation without disruptive influences caused by calcium-containing structures.

SUMMARY

This can be relevant, for example, for the evaluation of stenoses. As side-effects of the material breakdown, however, an unfavorable CT value shift, in particular, of fat-containing and air-containing volume elements, or an increase in image noise, can occur.

One or more example embodiments of the present invention provides an improved method and apparatus for generating a resultant image dataset of a patient, which at least partially addresses the side effects that arise.

Advantageous, and per se inventive, embodiments are the subject matter of the claims and the description below.

According to one or more example embodiments, a method for generating a resultant image dataset of a patient includes capturing a first image dataset of the patient based on a first X-ray quantum energy distribution and at least one second image dataset of the patient based on at least one second X-ray quantum energy distribution; first establishing a first spatial distribution of at least one first material in the patient based on the first image dataset and the at least one second image dataset via a basis material decomposition; second establishing background image datasets based on the first image dataset and the second image dataset, the established background image datasets including a background image dataset associated with the first X-ray quantum energy distribution and a background image dataset associated with the second X-ray quantum energy distribution; adapting values of the established background image datasets in regions in which the established first spatial distribution indicates a presence of the at least one first material, the adapting including applying a tissue image value associated with a respective X-ray quantum energy distribution to the values of the respective background image dataset corresponding to the X-ray quantum energy distribution, the adapting including, applying the adapted values to at least one of the first image dataset or the second image dataset; after the applying, third establishing a second spatial distribution of at least one second material in the patient based on the applying; and generating a resultant image dataset based on at least the second spatial distribution of the second material.

According to one or more example embodiments, the first establishing includes subtracting the tissue image value corresponding to the X-ray quantum energy distribution from the at least one of the first image dataset or the at least one second image dataset.

According to one or more example embodiments, the applying includes subtracting the respective adapted background image dataset corresponding to the X-ray quantum energy distribution from the at least one of the first image dataset or the at least one second image dataset.

According to one or more example embodiments, the at least one first material comprises calcium and the at least one second material comprises a contrast medium, and the first establishing and the third establishment includes a basis material decomposition into the at least one first material and the at least one second material, respectively.

According to one or more example embodiments, the second establishing includes a basis material decomposition into water and the at least one second material.

According to one or more example embodiments, the adapting includes replacing the values with the tissue image value corresponding to the X-ray quantum energy distribution or combining the values with the tissue image value in a weighted manner.

According to one or more example embodiments, the method further includes registering the first image dataset onto the second image dataset before the first establishing.

According to one or more example embodiments, the method further includes removing noise from (i) the first image dataset and the at least one second image dataset or (ii) the resultant image dataset.

According to one or more example embodiments, the third establishing includes establishing a further spatial distribution of the at least one first material, wherein the generating generates the resultant image dataset based on the established second spatial distribution of the second material and the established further spatial distribution.

According to one or more example embodiments, the respective tissue image value comprises an image value of blood or organ tissue.

According to one or more example embodiments, the respective tissue image value is selectable based on an imaging application or a medical problem.

According to one or more example embodiments, an apparatus for generating a resultant image dataset of a patient includes a first interface configured to capture a first image dataset of the patient dependent upon a first X-ray quantum energy distribution and at least one second image dataset of the patient dependent upon at least one second X-ray quantum energy distribution; a computation unit configured to first establish a first spatial distribution of at least one first material in the patient based on the first image dataset and the second image dataset via a basis material decomposition, second establish background image datasets based on the first image dataset and the second image dataset, the established background image datasets including a background image dataset associated with the first X-ray quantum energy distribution and a background image dataset associated with the second X-ray quantum energy distribution, adapt values of the established background image datasets in regions in which the established first spatial distribution indicates a presence of the at least one first material, wherein a tissue image value associated with one respective X-ray quantum energy distribution is applied to the values of the respective background image dataset corresponding to the X-ray quantum energy distribution, third establish a second spatial distribution of at least one second material in the patient based on the adapted values, and generate a resultant image dataset based on at least the second spatial distribution of the at least one second material; and a second interface configured to output the resultant image dataset.

According to one or more example embodiments, an imaging device includes the apparatus and at least one X-ray source arranged opposite to at least one X-ray detector, wherein a patient can be arranged between the X-ray source and the X-ray detector.

According to one or more example embodiments, a non-transitory computer program product has a computer program which can be directly loaded into a memory store of an apparatus configured to generate a resultant image dataset having program portions that, when executed by the apparatus, cause the apparatus to perform a method according to one or more example embodiments.

According to one or more example embodiments, a non-transitory computer-readable storage medium has program portions that, when executed by an apparatus configured to generate a resultant image dataset, cause the apparatus to perform a method according to one or more example embodiments.

BRIEF DESCRIPTION OF THE DRAWINGS

Exemplary embodiments will be described, making reference to the accompanying drawings. The illustrations in the figures are schematic, greatly simplified and not necessarily to scale. In the drawings.

DETAILED DESCRIPTION

Figure 1:
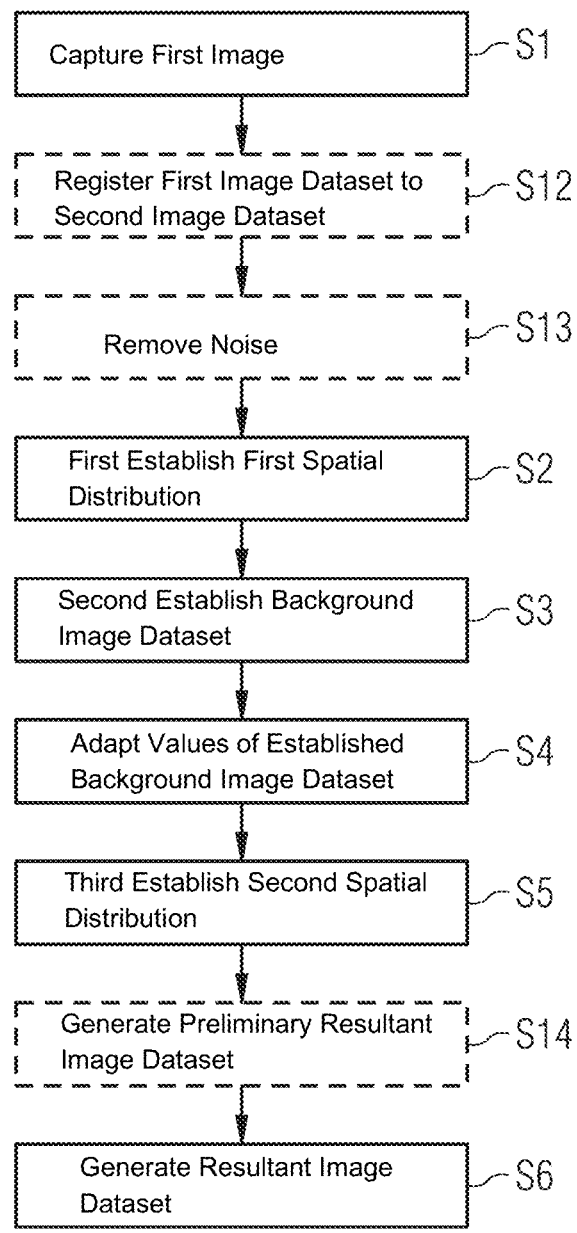
FIG. 1 is an exemplary sequence of a method for generating a resultant image dataset as a flow diagram according to an example embodiment.

One or more example embodiments of the present application relates to a method for generating a resultant image dataset of a patient comprising the steps of capturing, first establishment, second establishment, adapting, third establishment, generating and output.

The step of capturing comprises a capturing of a first image dataset of the patient dependent upon a first X-ray quantum energy distribution and at least one second image dataset of the patient dependent upon at least one second X-ray quantum energy distribution via a first interface. Thereby, a first image dataset is captured, representing a first X-ray attenuation distribution of the patient according to the first X-ray quantum energy distribution and at least one second image dataset representing at least one second X-ray attenuation distribution of the patient according to at least the second X-ray quantum energy distribution.

The image datasets can be generated with an imaging device according to one or more example embodiments of the present invention which is described in greater detail below, and in the step of capturing, are captured via the first interface for the further method steps of the method according to one or more example embodiments of the present invention. They can be present stored, for example, on a computer-readable storage medium or on a network or server and can be read out via the first interface in the step of capturing and can be captured for the further method steps of the method according to one or more example embodiments of the present invention.

The first image dataset and the second image dataset can be, in particular, tomographic image datasets which are established, i.e. reconstructed, on the basis of a plurality of projection datasets that have been recorded from different projection angles. They can be computed tomography image datasets which have been established via a computed tomography device. However, the first and the second image dataset can have been established by another radiographic means, for example via a C-arm X-ray device.

The result of such radiographic methods, for example computed tomography is the representation of the (X-ray) attenuation of an X-ray along its route from an X-ray source to an X-ray detector. This X-ray attenuation is caused by the irradiated media and/or materials along the ray path. The attenuation is typically defined as the logarithm of the ratio of the intensity of the attenuated radiation to the primary radiation and is denoted as an attenuation coefficient of the material in relation to a path-normal. In some radiographic imaging applications, but in particular in applications of computed tomography, rather than the attenuation coefficient itself, a value normalized to the attenuation coefficient of water, the CT number in Hounsfield units (HU), is used for representing the attenuation distribution of an X-ray beam in an examination object. This is calculated in a commonly known manner from an attenuation coefficient currently established by measurement and the reference attenuation coefficient of water. The first and/or second image dataset can reproduce, in particular, a spatial distribution of the attenuation coefficients and/or the CT number, i.e. the X-ray attenuation distribution of the patient. Since the two representations can be transformed into one another and/or are equivalent, in the following, the generally used expression X-ray attenuation distribution denotes both the distribution of the attenuation coefficient μ and also the distribution of the CT value.

The captured image datasets can relate to a subregion of the body of the patient, for example, a particular body region of the patient that is to be mapped via the resultant image dataset. In this case, the image datasets contain information regarding the X-ray attenuation distribution of the patient in relation only to the subregion being mapped, for example, in relation to the thorax or the pelvis. Alternatively, the image datasets relate to the whole body of the patient. In this case, the image datasets contain information regarding the X-ray attenuation distribution of the patient in relation to the whole body of the patient.

An X-ray quantum energy distribution denotes the energetic spectrum of the X-ray radiation that has been used for recording one of the image datasets. The at least two image datasets are generated with X-ray radiation having X-ray quantum energy distributions that differ from one another. The X-ray quantum energy distributions can differ, for example, in their mean X-ray quantum energy or in their peak energy and they can be spectrally partially overlapping or completely separate, and therefore have no overlap.

The at least two image datasets can be generated with a dual-energy or multi-energy imaging device. The different X-ray quantum energy distributions are therein generated by way of different accelerating voltages on the relevant X-ray source or sources of the X-ray image recording apparatus. Alternatively, the different X-ray quantum energy distributions can be generated with different spectral filters behind the X-ray source and/or with energy-selective detectors. Energy-selective should be understood to mean spectrally resolving and/or spectrally separating. Energy-selective detectors are configured to classify incident X-ray quanta according to their quantum energy. An energy-selective X-ray detector can be designed, in particular, as a photon-counting, direct-conversion X-ray detector.

The X-ray quantum energy distributions used for the recording of the image datasets can be specified and/or firmly set, in particular in advance, by the imaging device being used and its one or more accelerating voltages or other system parameters, for example, parameters of an energy-selective X-ray detector.

It is known that different materials and/or tissue types, for example water or bone, interact to a different extent with X-ray radiation. Furthermore, the energy-dependency of the X-ray attenuation on passing through material is also known. This means that low-energy X-ray radiation is more strongly absorbed by material than higher-energy X-ray radiation. The first image dataset thus represents the spatial X-ray attenuation distribution of the patient in relation to the first X-ray energy spectrum, i.e. the X-ray quantum energy distribution, and the at least one second image dataset represents the X-ray attenuation distribution of the patient in relation to the at least one second X-ray energy spectrum.

The step of the first establishment comprises an establishment of a first spatial distribution of at least one first material in the patient on the basis of the first and the at least one second image dataset via a computation unit. The first spatial distribution of the at least one first material can correspond substantially to a portion of the X-ray attenuation caused by the first material in the patient. It can correspond to a spatial density distribution for the first material and/or a concentration of the first material in the patient. The spatial distribution of the first material is suitable for representing visually the occurrence of the first material in the patient. The spatial distribution of the first material can reproduce spatially the proportion of the first material in the patient in a dataset with the same spatial dimensions as the first and/or second image dataset according to one or more example embodiments of the present invention. In particular, the first establishment of the first spatial distribution can comprise a basis material decomposition into at least the first and at least a second material on the basis of the first and the at least one second image dataset, so that in the step of the first establishment, a first spatial distribution of the first material and a first spatial distribution of the second material results. The spatial distribution of a second material can then substantially correspond to a portion of the X-ray attenuation caused by the second material in the patient. Advantageously, on the basis of the established first spatial distribution, a map of the first material can be provided, on the basis of which, regions in which the first material is present can advantageously be identified.

For the establishment of the spatial distribution, a per se known linear material and/or basis material decomposition into at least two materials can be carried out on the basis of the at least two image datasets. Material breakdown proceeds from the consideration that an X-ray attenuation value measured via an X-ray image recording apparatus can be described as a linear combination of X-ray attenuation values of so-called basic materials in relation to the aforementioned X-ray quantum energy distribution. Measured X-ray attenuation values result from the at least two image datasets at different X-ray quantum energy distributions. A material and/or basic material can be any substance or any desired tissue, in particular water, contrast medium such as iodine, soft tissue, bone and suchlike. The X-ray attenuation of a basic material dependent upon the energy of the X-ray radiation is, in principle, known or can be determined by way of prior measurements with phantoms and stored in the form of tables for retrieval in the context of the material breakdown. The result of the material breakdown can be a spatial distribution of the at least two materials in the patient, from which for each image element in the body region of the patient that is to be imaged, the basic material proportions and/or the basic material combination can be ascertained. Reference is made, by way of example, to W. Kalender et al. "Materialselektive Bildgebung und Dichtemessung mit der Zwei-Spektren-Methode, I. Grundlagen und Methodik" [Material-selective imaging and density measurement with the two-spectrum method, I. Principles and methods], W. Kalender, W. Bautz, D. Felsenberg, C. Süß und E. Klotz, Digit. Bilddiagn. 7, 1987, 66-77, Georg Thieme Verlag, in which a method for basis material decomposition in X-ray recordings is described. A basis material decomposition can be carried out in a manner that is obvious for a person skilled in the art, both in the image space and also in the projection space. The two procedures are equivalent in respect of the method according to one or more example embodiments of the present invention, although the computation steps in the image space can advantageously be carried out easily since a calculation can be performed image element by image element.

According to one or more example embodiments of the present invention, the first material comprises, in particular, calcium. The first material can be, for example, hydroxylapatite or another calcium-containing material which occurs, for example, in calcifications or in skeletal tissue in the human body. The second material can be, in particular, a contrast medium administered to the patient. A contrast medium should be understood in relation to the invention to be any medium which, after feeding into the examination object, in particular after injection into a patient leads to a contrast improvement or contrast enhancement in the absorption, that is in the X-ray image. Preferably, a contrast medium with an atomic number of greater than 20 or greater than 40 is used. The contrast medium has, in particular, an atomic number of less than 83 or less than 70. Particularly advantageously, contrast media contain, for example, iodine. However, a contrast medium can also be based upon gadolinium or another material. The first establishment of the first spatial distribution then comprises, in particular, a basis material decomposition into calcium and the contrast medium used. In this case, the generation of the first and the second at least one second image dataset of the patient takes place under contrast medium administration. In the event of a material breakdown into material comprising calcium and contrast medium in the context of the first establishment, on the basis of the first spatial distribution, material regions which are attributable to the calcium-containing material are advantageously to be distinguished from regions with contrast medium.

The establishment of the first spatial distribution of the first material can comprise, in particular, before a basis material decomposition, in each case, subtracting a tissue image value corresponding with regard to the X-ray quantum energy distribution from the first and the at least one second image dataset. This means that in this case, a tissue image value that can be associated with the first X-ray quantum energy distribution is subtracted from the first image dataset and a tissue image value that can be associated with the second X-ray quantum energy distribution is subtracted from the second image dataset. The tissue image value can serve as a tissue starting point for a subsequent linear basis material decomposition included by the first establishment. Via the subtraction of a tissue image value from the first and/or second image dataset before a basis material decomposition, a non-physical material breakdown in regions with materials that do not correspond to the basic material can be prevented. The tissue image value can be established, in particular, such that it characterizes tissue which is present or expected together with the first material in a region of the image datasets that is relevant for a diagnosis on the basis of the resultant image dataset. The tissue image value can, in particular, characterize tissue which is present or expected in combination with the first material or in the immediate vicinity of the first material in a relevant interesting region of the image datasets. The respective tissue image value can correspond to an image value for this tissue which would be expected in an image dataset mapping the tissue with the respective X-ray quantum energy distribution. The tissue image value can correspond to an image value to be expected for the tissue in the first and/or second image dataset dependent upon the first and/or second X-ray quantum energy distribution, said image value being retrievably provided in a database. An expected image value can be calculated making use of knowledge concerning the first and second X-ray quantum energy distribution and the known energy-dependent X-ray attenuation coefficient of the tissue material being used. Therein, an energetic hardening of the X-ray quantum energy distributions during passage through the patient can also be taken into account. For example, in simple embodiments, a factor dependent upon a patient diameter can be taken into account, on the basis of which an estimate for an easily adapted first and/or second X-ray quantum energy distribution can be obtained in order thereby to obtain an improved expectancy value for the respectively associated tissue image value. In a variant of the method, it is also conceivable that the respective tissue image value is also established directly from the first and/or second image dataset. If, for example, a particular structure, for example a plaque having a calcification, is to be evaluated via the resultant image dataset and if prior knowledge of the composition of this structure is available, it would be conceivable, on the basis of a segmentation of the structure and a material breakdown applied thereto into, firstly, the material of the calcification and a further known material that is present mainly in the relevant structure, to derive an existing portion of the further material and therefrom to derive an image value (dependent upon the X-ray quantum energy distributions) that is associated with the second material. This image value could then be applied, for example, as a better estimate for the tissue image value.

The tissue image value can be dependent, in particular, upon the medical problem under investigation and the region to be mapped resulting therefrom and/or the structure of interest in the patient. If the resultant image dataset serves, for example, for an evaluation of a stenosis and/or a plaque in a blood vessel of a patient, the tissue image value can correspond, in particular, to an image value of blood. It is assumed therein that blood flows through the structure. An alternative selection can be, for example, fat. If the focus of the resultant image dataset lies in the region of organ tissue, then the tissue image value can correspond, in particular, to an image value of the corresponding organ tissue. In particular, the tissue image value can be selectable by a user dependent upon a medical problem. It is therein conceivable that, through the selection of the medical problem under investigation and/or an associated imaging application, the tissue image value is established automatically. Advantageously, a generation of a resultant image dataset adapted to the medical problem is possible.

The step of the second establishment comprises an establishment of a background image dataset which can be associated with the first X-ray quantum energy distribution, and a background image dataset which can be associated with the second X-ray quantum energy distribution, via the computation unit and on the basis of the first and the second image dataset. The background image dataset can represent a general soft tissue image dataset or can at least approximately represent it. The second establishment can also comprise, in particular, a basis material decomposition on the basis of the first and the second image dataset. For example, a two-material breakdown into a target background material and an accompanying material, in particular a (target) background material and the second material can be carried out. The spatial distribution of the (target) background material resulting therefrom can then be converted making use of the knowledge regarding the first and the second X-ray quantum energy distribution and the known energy-dependent X-ray attenuation coefficient of the (target) background material into a background image dataset which can be associated with the first X-ray quantum energy distribution and a background image dataset which can be associated with the second X-ray quantum energy distribution. In this case also, hardening effects on the first and/or second X-ray quantum energy distribution can be taken into account on establishment of the background image datasets, for example, making use of a factor dependent upon the patient diameter.

Therein, advantageous results are obtained if the material breakdown for establishing the spatial distribution of the background material is based, apart from the background material, in particular also upon the second material for which in the subsequent step of the third establishment, a spatial distribution is established.

A spatial distribution of the background material can correspond in an advantageous implementation with a water-dependent portion of the X-ray attenuation caused by the patient. The background distribution can be established, for example, via a basis material decomposition into water and the second material, in particular a contrast medium that is used, for example iodine. In one variant, the background image dataset, which can be associated with the first X-ray quantum energy distribution, can correspond to the background image dataset which can be associated with the second X-ray quantum energy distribution. In this case, through the establishment of the one background image dataset, the other background image dataset is also established. This can be the case, in particular, if water is selected as the background material, so that the background image dataset is the same, by definition, for all the X-ray quantum energy distributions, provided the CT values are calculated in HU units.

Advantageously, via known methods, a background image dataset can be provided for further use in the subsequent method steps which can ultimately be used to obtain an advantageous material breakdown and to prevent unwanted image displacements.

The step of adapting comprises an adaptation of values of the established background image dataset via the computation unit in regions in which the established first spatial distribution indicates the presence of the first material, wherein the tissue image value that can be associated in each case with the one respective X-ray quantum energy distribution is applied to the values of the background image dataset respectively corresponding with regard to the X-ray quantum energy distribution. The tissue image value applied here corresponds, in particular, to the tissue image value already described in relation to the first establishment. The tissue upon which the respective tissue image value is based comprises, in particular, a different material from the background material. In particular, in the step of adapting, values of the established background image dataset which can be associated with the first X-ray quantum energy distribution are adapted, via the tissue image value which corresponds with regard to the X-ray quantum energy distribution, i.e. which can also be associated with the first X-ray quantum energy distribution. Furthermore, values of the established background image dataset which can be associated with the second X-ray quantum energy distribution are adapted, via the tissue image value which corresponds with regard to the X-ray quantum energy distribution, i.e. which can also be associated with the second X-ray quantum energy distribution.

Identification of the regions which are to be associated with the first material is therein particularly easily possible making use of the established first spatial distribution of the first material, since herein an improved differentiability of the first material, for example, the differentiation between a first material having calcium and a contrast medium that is also present, is possible exactly and easily. For the identification of the regions in which the established first spatial distribution indicates the presence of the first material, a segmentation method can be applied to the first spatial distribution. The segmentation can be achieved, for example, pixel-based, voxel-based, edge-based, area-based and/or region-based. The segmentation can also be based upon a model-based method, wherein assumptions regarding the object to be segmented are used. The segmentation can be implemented by the computation unit automatically or semi-automatically. For example, starting points or kernels or coarse contour information item for the segmentation can be set manually. In a preferred simple implementation, a threshold value-based segmentation method is utilized wherein the values of the first spatial distribution are compared with at least one threshold value. Based thereon, a differentiation can be brought about as to whether a space point of the spatial distribution is to be associated to a high degree of probability with the first material or not. In order to enhance the specificity or sensitivity, optionally further intermediate images calculated from the first spatial distribution can be formed, for example, via a grey value dilation, to which likewise, a suitably selected threshold value is applied. On the basis of such a segmentation, for example, a binary map mapping the spatial occurrence of the first material in the patient can be provided, via which in a simple manner, the regions which are to be associated with the first material are identifiable in the background map.

The adaptation of the values of the established background image dataset can comprise in each case, in particular, in the regions where the established first spatial distribution indicates the presence of the first material, replacing the values of the background image dataset with the respectively determined tissue image value or replacing them at least weighted, i.e. combining the values of the background image dataset with the tissue image value. Therein, in particular in edge regions of the identified regions, a weighted replacement can be advantageous, so that hard edges between the replaced regions and the surrounding regions of the background image dataset are prevented. By way of example, a truncated Gaussian filter can be used for a weighted combination. The background image dataset is modified, in particular, where on the basis of the result of the first establishment, the first material exists with a high probability. It can thereby be achieved that particularly in these regions, the most detailed possible breakdown can take place in the third establishment, as described below, and transition artifacts occurring in the resultant image are suppressed.

The step of the third establishment comprises an establishment of a second spatial distribution of at least one second material in the patient on the basis of the first and the at least one second image dataset via the computation unit. The second spatial distribution of the second material can substantially correspond to a portion of the X-ray attenuation caused by the second material in the patient. Therein, before the third establishment, in each case, the adapted background image dataset corresponding with regard to the X-ray quantum energy distribution, is applied to the first and/or at least one second image dataset. This means that the adapted background image dataset that can be associated with the first X-ray quantum energy distribution is applied to the first image dataset and the adapted background image dataset that can be associated with the second X-ray quantum energy distribution is applied to the second image dataset.

The application of the adapted background image dataset to the first and/or the at least one second image dataset can comprise combining the spatially corresponding values of a respective background image dataset and a respective first and/or second image dataset. In particular, the application of the adapted background image dataset to the first and/or at least one second image dataset can comprise subtracting the respective adapted background image dataset from the first and/or the at least one second image dataset.

In the step of the third establishment, apart from the second spatial distribution of the second material, a further spatial distribution of the first material, i.e. a second spatial distribution of the first material can be established.

In particular, both the first and also the third establishment can comprise a basis material decomposition into at least the first and the second material, so that in each case, a spatial distribution of the first material and a spatial distribution of the second material results. In particular, the first material can therein comprise calcium and the second material can comprise a contrast medium used for the generation of the image datasets, for example, iodine, wherein the first establishment of the first spatial distribution and the third establishment of the second spatial distribution then comprises a basis material decomposition into the material containing calcium and the contrast medium. In particular, the establishment of the background image dataset can comprise a basis material decomposition into water and the contrast medium that is used. The application of the method according to one or more example embodiments of the present invention to a material having calcium, for example hydroxylapatite and a contrast medium represents a particularly important application case, for example in the assessment of plaques and/or stenoses.

The step of generating comprises a generation of a resultant image dataset on the basis of at least the second spatial distribution of the second material via the computation unit. The generation can comprise merely the retrievable provision of the second spatial distribution of the second material in the form of a spatial representation. Thus, the second spatial distribution can correspond substantially directly to the resultant image dataset which can be output via a second interface. However, further processing steps based upon the second spatial distribution can also be included by the step of generation. If, in the step of the third establishment, apart from the second spatial distribution of the second material, a further spatial distribution of the first material, i.e. the second spatial distribution of the first material is also established, a resultant image dataset can be generated on the basis of the established second spatial distribution of the second material and the established second spatial distribution of the first material. For example, a weighted mixed image can be generated. For example, a so-called virtual monoenergetic image (VMI) on the basis of the established second spatial distribution of the second material and the established further, i.e. second, spatial distribution of the first material can be calculated and output as a resultant image dataset. A method of this type has been disclosed, for example, in DE 10 2015 204 450 A1, the entire contents of which are hereby incorporated by reference.

In particular, in the step of generation, as the resultant image dataset, a representation of the patient in which the first material is removed or is at least partially suppressed can be provided at least on the basis of the spatial distribution of the second material. By way of example, in the step of the third establishment, a representation of the patient can be generated, at least on the basis of the spatial distribution of the second material, for example iodine, in which the first material, for example in particular, calcifications is removed. Via the method according to one or more example embodiments of the present invention, it is advantageously achieved that in this representation the attenuation caused by the first material is removed without the attenuation caused by the second material, i.e. the image values corresponding to the attenuation caused by the second material, being influenced. Furthermore, particularly advantageously, image value displacements in regions with materials that are not basic materials are prevented. This applies, for example, to a contrast inversion in the presence of fat or air. The advantages are achieved, in particular, by way of the advantageous establishment and application of the background map adapted according to one or more example embodiments of the present invention before the third establishment. Therein, the application, in particular a subtraction, of the respectively adapted background map before carrying out a material breakdown during the third establishment corresponds to a projection of the image values of the first and/or second image dataset onto the material vector of the second material. It can be achieved by way of the specific generation of the background map that particularly in relevant regions in which the first material is present, a particularly detailed breakdown is carried out and otherwise frequently occurring transition artifacts in the resultant image can advantageously be suppressed.

According to one or more example embodiments of the present invention, before the first establishment of the first spatial distribution of the first material, a registration of the first image dataset onto the second image dataset can take place. This can then lead in particular to advantageously improved results if the first and second image dataset do not represent exactly the same time and the same location and a movement of the recorded object at the time point of the recording of the first and the second image dataset cannot be precluded. This is the case, in particular for example, if the first image dataset and the second image dataset have been recorded via a so-called dual-energy method using two X-ray spectra. Particularly advantageously, this can be precluded by the use of an energy-selective, i.e. energy-resolving, X-ray detector which is designed to record simultaneously the data for the first and for the second image dataset in a first energy region, i.e. according to a first X-ray quantum energy distribution, and a second energy region, i.e. according to a second X-ray quantum energy distribution.

A registration should be understood to mean a method with which, given two images which reproduce the same or a similar subject matter, an unambiguous topographic relationship or correlation is created between their image elements (pixels and/or voxels). The establishment of the correlation usually takes place via distinctive features, so-called landmarks, which are established either interactively by a user or automatically by a system. The landmarks can be one-dimensional structures such as special anatomical points or multi-dimensional structures such as surfaces of particular organs that have previously been segmented in the images. The registration can however also take place via intensity value distributions stored in the images. The image registration is a common task in medical image processing for which there are numerous proposed solutions. Examples of usable optimization methods for registration methods are gradient descent methods, downhill simplex methods, hill climbing methods and simulated annealing. For the registration, in particular, a non-rigid, flexible or elastic registration can be used. An elastic registration method should be understood to be an image registration method in which elastic transformations, also called "non-rigid transformations" such as spline or polynomial-based transformations are usable.

In particular, in an advantageous embodiment of the invention, before the first establishment of the first spatial distribution, a method of noise removal can be applied to the first and the at least second image dataset and/or a method of noise removal can be applied to the resultant image dataset, at least in regions in which the established first spatial distribution indicates the presence of the first material. The application of a method for noise removal to the resultant image dataset can involve, before the generation and output of a final resultant image dataset, a preliminary resultant image dataset being generated via the computation unit, based upon at least the second spatial distribution of the second material, wherein a method of noise removal is applied to the preliminary resultant image dataset, at least in regions in which the established first spatial distribution indicates the presence of the first material. The preliminary resultant image dataset can correspond to the (final) resultant image dataset, wherein only the application of the noise removal method differentiates the preliminary resultant image dataset from the (final) resultant image dataset. For the generation of a final resultant image dataset, further processing steps can also follow after the application of the noise removal method, for example the generation of a weighted mixed image as described above.

A method of noise removal is, in particular, a noise-reducing method. In the noise-reducing methods there exist both those which treat a single image dataset as well as those which treat a plurality of correlated image datasets simultaneously or calculate, from a combination of the image datasets to be treated, an intermediate result which is used as a side channel in the noise removal of all the image datasets. Preferably, a method of noise removal is used which functions in an edge-preserving manner. Preferably, a method is used which functions with multi-spectrally generated image datasets, i.e. at least two image datasets, each on the basis of a different X-ray quantum energy distribution. Preferably, a method as described in the application DE 10 2019 210 355 A1 can be used, the entire contents of which are herein incorporated by reference. For instance, a method as described in the applications DE 10 2009 010 501 A1 or DE 10 2008 063 311 A1 can be used, the entire contents of each of which are herein incorporated by reference.

Advantageously, the first establishment of the first spatial distribution on the basis of noise-removed image datasets can supply improved and more robust results. Advantageously, an adaptation of the background image datasets in regions in which the established first spatial distribution indicates the presence of the first material, can be carried out in a better way, since erroneously identified regions can be better prevented.

In the resultant image dataset, in particular in regions in which the established first spatial distribution indicates the presence of the first material, an increased noise level can occur. Advantageously, via a method of noise removal, an increased noise level in the resultant image dataset, in particular in regions in which the established first spatial distribution indicates the presence of the first material, can be prevented. Advantageously, the strength of the noise removal is therein adapted to the surroundings of the regions in which the established first spatial distribution indicates the presence of the first material so that the final noise level in the resultant image dataset is uniform. Advantageously, a particularly high quality resultant image dataset can be achieved on the basis at least of the second spatial distribution of the second material. In particular, the second spatial distribution can herein correspond to a preliminary resultant image dataset to which the method of noise reduction is applied.

One or more example embodiments of the present invention further relates to an apparatus for generating a resultant image dataset of a patient, comprising a first interface, a computation unit and a second interface.

The first interface is designed to capture a first image dataset of the patient dependent upon a first X-ray quantum energy distribution and at least one second image dataset of the patient dependent upon at least one second X-ray quantum energy distribution. This means that the first interface is designed to capture a first image dataset of the patient representing a first X-ray attenuation distribution of the patient according to a first X-ray quantum energy distribution and at least one second image dataset of the patient representing at least one second X-ray attenuation distribution of the patient according to at least one second X-ray quantum energy distribution.

The computation unit is designed for the first establishment of a first spatial distribution of at least one first material in the patient on the basis of the first and the at least one second image dataset. The computation unit is further designed for the second establishment of a background image dataset which can be associated with the first X-ray quantum energy distribution, and a background image dataset which can be associated with the second X-ray quantum energy distribution, on the basis of the first and the second image dataset. The computation unit is also designed to adapt values of the background image datasets in regions in which the established first spatial distribution indicates the presence of the first material, wherein a tissue image value that can be associated with a respective X-ray quantum energy distribution is applied to the values of the respective spatial background image dataset corresponding with regard to the X-ray quantum energy distribution, for the third establishment of a second spatial distribution of at least one second material in the patient on the basis of the first and the second image dataset, wherein before the third establishment, in each case, the adapted background image dataset corresponding with regard to the X-ray quantum energy distribution is applied to the first and/or at least one second image dataset, and for generating the resultant image dataset on the basis of at least the second spatial distribution of the second material.

The second interface is configured to output the resultant image dataset.

Such an apparatus for generating a resultant image dataset can be designed, in particular, to carry out the inventive method according to one or more example embodiments of the present invention for generating a resultant image dataset and its aspects as described above. The apparatus can be designed to carry out the methods and their aspects in that the interfaces and the computation unit are designed for carrying out the corresponding method steps.

In particular, the computation unit can be designed in the context of the first establishment and the third establishment, in each case, to carry out a basis material decomposition into the first and the second material. In particular, the computation unit can be designed in the context of the second establishment, to carry out a basis material decomposition into a background material and, for example, the second material.

The apparatus and/or the computation unit can be, in particular, a computer, a microcontroller or an integrated circuit. Alternatively, it can be a real or virtual grouping of computers (a technical term therefor being "cluster" or, in the case of a virtual grouping, "cloud"). The apparatus can also be designed as a virtual system which is executed on a real computer or a real or virtual grouping of computers (a technical term therefor being "virtualization").

An interface can be a hardware or software interface (for example, PCI bus, USB or Firewire). A computation unit can have hardware elements or software elements, for example, a microprocessor or a so-called FPGA (Field Programmable Gate Array).

The interfaces can comprise, in particular, a plurality of sub-interfaces. In other words, the interfaces can also comprise a plurality of interfaces. The computer unit can also comprise, in particular, a plurality of subsidiary computation units which carry out different steps of the respective method. In other words, the computation unit can also be regarded as a plurality of computation units.

The apparatus can also comprise a storage unit. A storage unit can be realized as a non-permanent working memory (Random Access Memory (RAM)) or as a permanent mass storage unit (hard disk, USB stick, SD card, solid state disk).

The advantages of the proposed apparatus substantially correspond to the advantages of the proposed method for generating a resultant image dataset. Features, advantages or alternative embodiments mentioned herein can also be transferred to the apparatus and vice versa.

One or more example embodiments of the present invention further relates to an imaging device comprising an apparatus for generating a resultant image dataset and comprising at least one X-ray source arranged opposite to at least one X-ray detector, wherein a patient can be arranged between the X-ray source and the X-ray detector.

Therein the imaging device is advantageously designed for carrying out an embodiment of the proposed method for generating a resultant image dataset. The advantages of the proposed imaging device substantially correspond to the advantages of the proposed method for generating a resultant image dataset. Features, advantages or alternative embodiments mentioned herein can also be transferred to the imaging device and vice versa.

The imaging device can be, in particular, an X-ray device which is designed for recording a plurality of X-ray projections from different projection angles, for example, a computed tomography device with a ring-shaped rotary frame, or a C-arm X-ray device. The recordings can be generated during an, in particular, continuous rotation movement of a recording unit comprising the X-ray source and the X-ray detector cooperating with the X-ray source. An X-ray source can be, in particular, an X-ray tube with a rotary anode. An X-ray detector for a computed tomography device is, for example, a linear detector with a plurality of lines. An X-ray detector for a C-arm X-ray device is, for example, a planar detector.

The X-ray detector can be a spectrally separating X-ray detector. It is configured to classify incident X-ray quanta according to their quantum energy and to assign each of them to one of the image datasets. In this way, only one X-ray source with a pre-determined and/or fixed emission spectrum is needed for the method according to one or more example embodiments of the present invention. According to this aspect, the recording of the image datasets takes place particularly rapidly and without an additional dosage burden on the patient. The X-ray detector can be a quantum-counting detector or a two-layer detector. A quantum-counting detector should typically be understood to be a directly-converting detector which directly converts an incident X-ray quantum via suitable detector material into an electrical signal. Quantum-counting detectors can be operated in an energy-resolving manner, wherein the energy resolution is settable via so-called binning. In other words, any desired energy regions can be specified, in relation to which incident X-ray quanta can be classified. The first and the at least one second image dataset are each formed by signals within one or more energy regions. The association of energy regions with the image datasets can take place dependent upon the first and/or at least one second X-ray quantum energy distribution. Detector materials that are suitable for quantum-counting detectors are, in particular, the semiconductors cadmium telluride, cadmium zinc telluride or gallium arsenide or, in the case of a planar detector, amorphous selenium or suchlike. A two-layer detector or a dual or double layer detector is designed to analyze the incident X-ray tube spectrum into a low energy portion and a high energy portion. For this purpose, the two-layer detector is constructed from two layers. A detector layer facing toward the X-ray radiation source measures photons of the incident X-ray radiation with a low energy and allocates the measured signals to the first image dataset. It is penetrated by high-energy X-ray radiation. Photons with a higher quantum energy are measured in the detector layer arranged thereunder and/or therebehind, that is, facing away from the X-ray radiation source and are allocated to the second image dataset. Typically, both detector layers comprise a scintillator and consequently, the two-layer detector is an indirectly converting detector. Crystals such as cesium iodide, cadmium tungstate or ceramic substances such as, for example, gadolinium oxysulfide or suchlike are used as the scintillator material.

The imaging device can also comprise two source-detector systems which function with different emission spectra. In this case, the imaging device comprises two X-ray radiation sources and two X-ray detectors, wherein each detector is configured for recording the X-ray radiation emitted by one of the X-ray sources. This is also referred to as a dual-source X-ray imaging apparatus. At least one of the two X-ray sources can also comprise a filter for improving the spectral separation of the outgoing X-ray radiation, in particular a tin filter.

The imaging device can also be configured for so-called kV switching, wherein the X-ray source emits different emission spectra in the direction of an X-ray detector in quick succession.

One or more example embodiments of the present invention further relates to a computer program product with a computer program which is loadable directly into a memory store of an apparatus for generating a resultant image dataset, having program portions in order to carry out all the steps of a method for generating a resultant image dataset, as described above, and its aspects when the program portions are executed by the apparatus.

A computer program product can be a computer program or can comprise a computer program. In this way, the inventive method according to one or more example embodiments of the present invention can be carried out rapidly, exactly reproducibly and robustly. The computer program product is configured such that it can carry out the method steps according to one or more example embodiments of the present invention via the apparatus. The apparatus must have the respective pre-conditions such as, for example, a corresponding working memory store, a corresponding graphics card or a corresponding logic unit so that the respective method steps can be carried out efficiently. The computer program product is stored, for example, on a computer-readable medium or is deposited on a network or server from where it can be loaded into a computation unit of the apparatus.

One or more example embodiments of the present invention relates to a computer-readable storage medium on which program portions that are readable and executable by the apparatus for generating a resultant image dataset are stored, in order to carry out all the steps of one of the methods described above for generating a resultant image dataset or its aspects when the program portions are executed by the apparatus.

Examples of a computer-readable storage medium are a DVD, a magnetic tape, a hard disk drive or a USB stick, on which electronically readable control information, in particular software, is stored.

A realization largely through software has the advantage that conventionally used apparatuses and computation units can easily be upgraded with a software update in order to operate in the manner according to one or more example embodiments of the present invention. A computer program product can comprise, apart from the computer program, possibly additional constituents, such as, for example, documentation and/or additional components as well as hardware components, for example, hardware keys (dongles, etc.) for using the software.

In the context of the invention, features which are described in relation to different embodiments of the invention and/or different claim categories (method, use, apparatus, system, arrangement, etc.) can, in particular, also be combined to further embodiments of the invention. For example, a claim which relates to an apparatus, can also be developed with features which are described or claimed in relation to a method and vice versa. Functional features of a method can be carried out via correspondingly configured physical components.

The use of the indefinite article "a" or "an" does not preclude that the relevant feature can also be present plurality. The use of the expression "have" does not preclude that the concepts linked via the expression "have" can be identical. For example, the medical imaging apparatus has the medical imaging apparatus. The use of the expression "unit" does not preclude that the subject matter to which the expression "unit" relates can have a plurality of components that are spatially separated from one another.

The expression "based upon" can be understood in the context of the present application, in particular, in the sense of the expression "using". In particular, a formulation according to which a first feature is generated (alternatively: established, determined, etc.) based upon a second feature does not preclude the first feature being generated (alternatively: established, determined, etc.) based upon a third feature.

FIG. 1 shows an exemplary sequence of a method for generating a resultant image dataset of a patient 39 as a flow diagram.

The method comprises the capturing S1 of a first image dataset of the patient 39 representing a first X-ray attenuation distribution of the patient 39 according to a first X-ray quantum energy distribution and at least one second image dataset of the patient 39 representing at least one second X-ray attenuation distribution of the patient 39 according to at least one second X-ray quantum energy distribution via a first interface 21. The image datasets can be generated with an imaging device according to one or more example embodiments of the present invention, as shown, for example, in FIG. 3 and are captured via the interface and are thus provided for the further method steps. The first image dataset and the second image dataset can be, in particular, tomographic image datasets which are established, i.e. reconstructed, on the basis of a plurality of projection datasets that have been recorded from different projection angles. The captured image datasets can relate to a subregion of the body of the patient 39, for example, a particular body region of the patient 39 that is to be mapped via the resultant image dataset. If, for example, a stenosis of a blood vessel of the patient is to be assessed making use of the resultant image dataset, then the first and the second image dataset comprises at least the region of the stenosis, exactly like the resultant image dataset.

Optionally, in a step S12, a registration of the first image dataset to the second image dataset can take place. This can then lead, in particular, to advantageously improved results if the first and second image dataset do not represent exactly the same time and the same location and a movement of the recorded object at the time point of the recording of the first and the second image dataset cannot be precluded. For the registration, in particular, a non-rigid, flexible or elastic registration can be used.

Furthermore, a method of noise removal can optionally be applied to the first and the second image dataset in a step S13. Preferably, therein a method for noise removal is used which operates in an edge-preserving manner and with multi-spectrally generated image datasets, i.e. at least two image datasets, each on the basis of a different X-ray quantum energy distribution. Preferably a method as described in the application DE 10 2019 210 355 A1 is used. Advantageously, the subsequent first establishment of the first spatial distribution on the basis of noise-removed image datasets can ensure an improved identification of regions in which the established first spatial distribution indicates the presence of the first material.

In a further step S2, the first establishment of a first spatial distribution of at least one first material in the patient 39 takes place on the basis of the, optionally noise-removed, first and the at least one, optionally noise-removed, second image dataset via a computation unit 23. The first spatial distribution of the at least first material can correspond substantially to a portion of the X-ray attenuation caused by the first material in the patient 39. In particular, the first establishment comprises a linear basis material decomposition into at least the first material on the basis of the first and the second image dataset. In particular, a linear basis material decomposition into the first material and the second material that is relevant for the step of the third establishment is carried out so that in the step of the first establishment, a first spatial distribution of the first material and a first spatial distribution of the second material results. Advantageously, on the basis of the established first spatial distribution of the first material, a map of the first material can be provided, on the basis of which, regions in which the first material is present and which can particularly suitably be delineated from the second material can advantageously be identified. For example, the first material comprises, in particular, calcium or corresponds to hydroxylapatite. In particular, the first establishment S2 comprises a basis material decomposition into a material having calcium as the first material and a contrast medium, in particular iodine, as the second material.

The first establishment S2 can therein comprise, before the basis material decomposition, in each case, subtracting a tissue image value, corresponding with regard to the X-ray quantum energy distribution, from the first and the at least one second image dataset. This means that a tissue image value that can be associated with the first X-ray quantum energy distribution is subtracted from the first image dataset and a tissue image value that can be associated with the second X-ray quantum energy distribution is subtracted from the second image dataset. The tissue image value serves as a tissue output point for a subsequent linear basis material decomposition, wherein a non-physical material breakdown in regions with materials that do not correspond to basic materials which do not underlie the basis material decomposition is prevented. The tissue image value can, in particular, characterize tissue which is present or expected in combination with the first material or in the immediate vicinity of the first material in a relevant region of interest of the image datasets. For example, this can involve blood or fat. The tissue image value can be dependent, in particular, upon a medical problem of interest. The tissue image value can be capable of being selected by a user dependent upon an application/medical problem. For example, a tissue image value that is to be expected dependent upon the first and/or second X-ray quantum energy distribution can be retrievably provided in a database and retrieved in the context of the method. Therein, hardening effects on the first and/or second X-ray quantum energy distribution by way of the patient can be taken into account.

In a further step S3, a second establishment of a background image dataset which can be associated with the first X-ray quantum energy distribution, and a background image dataset which can be associated with the second X-ray quantum energy distribution, is carried out via the computation unit 23 on the basis of the first and the second image dataset. The background image dataset can represent a general soft tissue image dataset or can at least approximately represent it. For example, the background image dataset can correspond in particular to a water-dependent portion of the X-ray attenuation caused by the patient 39. The second establishment can also comprise, in particular, a basis material decomposition on the basis of the first and the second image dataset. For example, a two-material breakdown into a target background material and advantageously, the second material can be carried out. The spatial distribution of the (target) background material resulting therefrom can then be converted making use of the knowledge regarding the first and the second X-ray quantum energy distribution and the known energy-dependent X-ray attenuation coefficient of the (target) background material into a background image dataset which can be associated with the first X-ray quantum energy distribution and a background image dataset which can be associated with the second X-ray quantum energy distribution. In this case also, hardening effects on the first and/or second X-ray quantum energy distribution can be taken into account in the establishment of the background image datasets, for example, making use of a factor dependent upon the patient diameter.

In a step S4, an adaptation of values of the established background image dataset via the computation unit takes place in regions in which the established first spatial distribution indicates the presence of the first material, wherein the tissue image value that can be associated in each case with the one respective X-ray quantum energy distribution is applied to the values of the spatial background image dataset corresponding with regard to the X-ray quantum energy distribution. The tissue image value applied here corresponds, in particular, to the tissue image value already described in relation to the first establishment. The adaptation of the values of the established background image dataset can comprise in each case, in particular, in the regions where the established first spatial distribution indicates the presence of the first material, replacing the values of the background image dataset with the respectively determined tissue image value or replacing them at least weighted, i.e. combining the values of the background image dataset with the tissue image value. Identification of the regions which are to be associated with the first material is therein particularly easily possible making use of the established first spatial distribution of the first material, since herein an improved differentiability of the first material in the image dataset, for example, the differentiation between a first material having calcium and a contrast medium that is also present, is possible exactly and easily. For the identification of the regions in which the established first spatial distribution indicates the presence of the first material, a segmentation method can be applied to the first spatial distribution.

In a step S5, a third establishment of a second spatial distribution of at least one second material in the patient 39 takes place on the basis of the first and the second image dataset via a basis material decomposition via the computation unit 23. Therein before the third establishment, the adapted background image dataset that can be associated with the first X-ray quantum energy distribution is applied to the first image dataset, in particular subtracted therefrom, and the adapted background image dataset that can be associated with the second X-ray quantum energy distribution is applied to the second image dataset, in particular subtracted therefrom. In particular, both the first and also the third establishment can comprise a basis material decomposition into at least the first and the second material, so that in each case, a spatial distribution of the first material and a spatial distribution of the second material results. In particular, the first material can therein comprise calcium and the second material can comprise a contrast medium used for the generation of the image datasets, for example, iodine, wherein the first establishment of the first spatial distribution and the third establishment of the second spatial distribution then comprises a basis material decomposition into the material containing calcium and the contrast medium.

In a step S6, a generation of a resultant image dataset takes place on the basis of at least the second spatial distribution of the second material via the computation unit 23 and subsequent output of the resultant image dataset via a second interface 27. The generation can comprise merely the retrievable provision of a spatial representation of the second spatial distribution of the second material as a resultant image dataset. Thus, the second spatial distribution can correspond substantially directly to the resultant image dataset which can be output via a second interface. However, further processing steps based upon the second spatial distribution can also be included by the step of generation. If, in the step of the third establishment, apart from the second spatial distribution of the second material, a further spatial distribution of the first material, i.e. the second spatial distribution of the first material is also established, a resultant image dataset can be generated on the basis of the established second spatial distribution of the second material and the established second spatial distribution of the first material. For example, a weighted mixed image can be generated. For example, a so-called virtual monoenergetic image (VMI) on the basis of the established second spatial distribution of the second material and the established further, i.e. second, spatial distribution of the first material can be calculated and output as a resultant image dataset.

In particular, in the step of generating, as the resultant image dataset, a representation of the patient in which the first material is removed or is at least partially suppressed can be provided at least on the basis of the spatial distribution of the second material. For example, in the step of the third establishment, a representation of the patient can be generated, at least on the basis of the spatial distribution of the second material, for example iodine, in which the first material, for example in particular calcifications, is removed. The application of the method to the materials iodine and contrast medium relates to application fields in which, in particular, both materials are present in the region to be mapped, in particular also in the direct vicinity thereof and a precise differentiation of the calcium-containing image components and the contrast medium-containing image components is to be separated and/or differentiated from one another. In particular, a representation of calcium-removed image datasets can be striven for in order to enable an improved evaluation of calcified plaques and stenoses resulting therefrom. However, other fields of use can also exist.

Optionally, in step S14, before the establishment and output of the final resultant image dataset, a preliminary resultant image dataset is generated via the computation unit 23, based upon at least the second spatial distribution of the second material, wherein a method of noise removal can be applied to the preliminary resultant image dataset, at least in regions in which the established first spatial distribution indicates the presence of the first material. The preliminary resultant image dataset can correspond to the (final) resultant image dataset, wherein only the application of the noise removal method differentiates the preliminary resultant image dataset from the (final) resultant image dataset. For the generation of a final resultant image dataset, further processing steps can follow the application of the noise removal method, for example, the generation of a weighted mixed image as described above. Preferably, a method of noise removal as described in the application DE 10 2019 210 355 A1 can be used.

Figure 2:
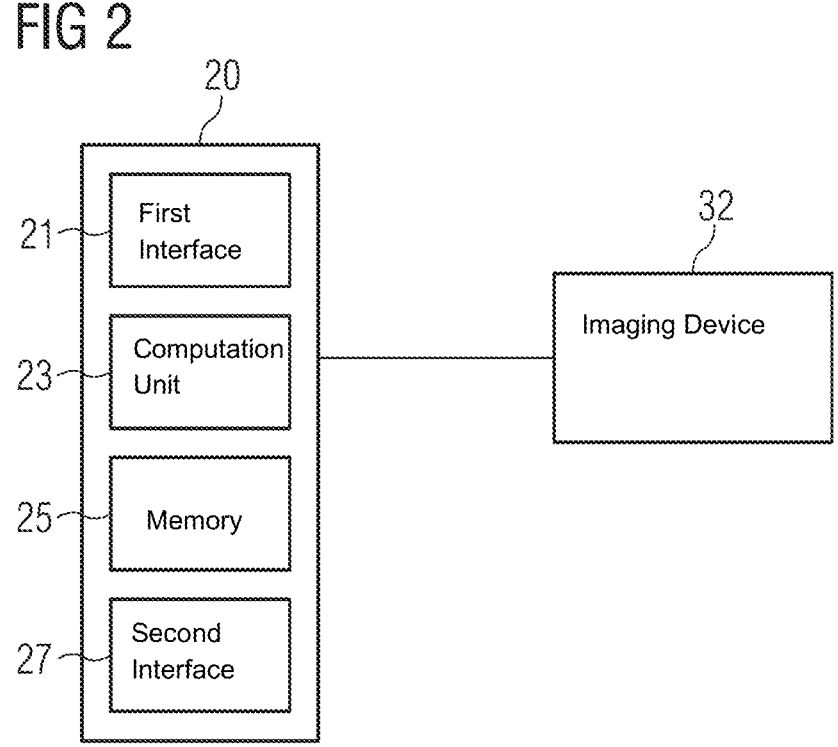
FIG. 2 is an exemplary schematic representation of an apparatus for generating a resultant image dataset according to an example embodiment.

FIG. 2 shows an apparatus 20 for generating a resultant image dataset of a patient 39, comprising a first interface 21 designed for capturing a first image dataset of the patient 39 representing a first X-ray attenuation distribution of the patient 39 according to a first X-ray quantum energy distribution and at least one second image dataset of the patient 39 representing at least one second X-ray attenuation distribution of the patient 39 according to at least one second X-ray quantum energy distribution.

The apparatus further comprises a computation unit 23, which is designed
for first establishment S2 of a first spatial distribution of at least one first material in the patient 39 on the basis of the first and the second image dataset via a basis material decomposition,
for second establishment S3 of a background image dataset which can be associated with the first X-ray quantum energy distribution, and a background image dataset which can be associated with the second X-ray quantum energy distribution, on the basis of the first and the second image dataset, for adapting S4 values of the established background image datasets in regions in which the established first spatial distribution indicates the presence of the first material, wherein a tissue image value that can be associated in each case with the one respective X-ray quantum energy distribution is applied to the values of the established background image dataset corresponding with regard to the X-ray quantum energy distribution,
for third establishment S5 of a second spatial distribution of at least one second material in the patient 39 on the basis of the first and the second image dataset via a basis material decomposition wherein, before the third establishment, in each case, the adapted background image dataset corresponding with regard to the X-ray quantum energy distribution, is applied to the first and/or at least one second image dataset, and
for generating S7 the resultant image dataset on the basis of at least the second spatial distribution of the second material.

The apparatus further comprises a second interface 27, which is designed to output the resultant image dataset, and a memory 25.

In the exemplary embodiment shown, the apparatus is connected to an imaging device 32. The apparatus can be connected, for example, via a network to the imaging device. In particular, the apparatus can also be included by the imaging device 32. The imaging device can be, for example, a computed tomography device.

The network can be a local network (examples being a local area network (LAN) or a wide area network (WAN)). An example of a local area network is an Intranet, an example of a wide area network is the Internet. The network can, in particular, also be configured to be wireless, in particular, as a WLAN (wireless LAN), also called WiFi, or as a Bluetooth connection. The network can also be designed as a combination of the aforementioned examples.

Furthermore, a communication between the apparatus and an imaging device 32 can also take place offline, for example, by way of an exchange of data carriers.

Figure 3:
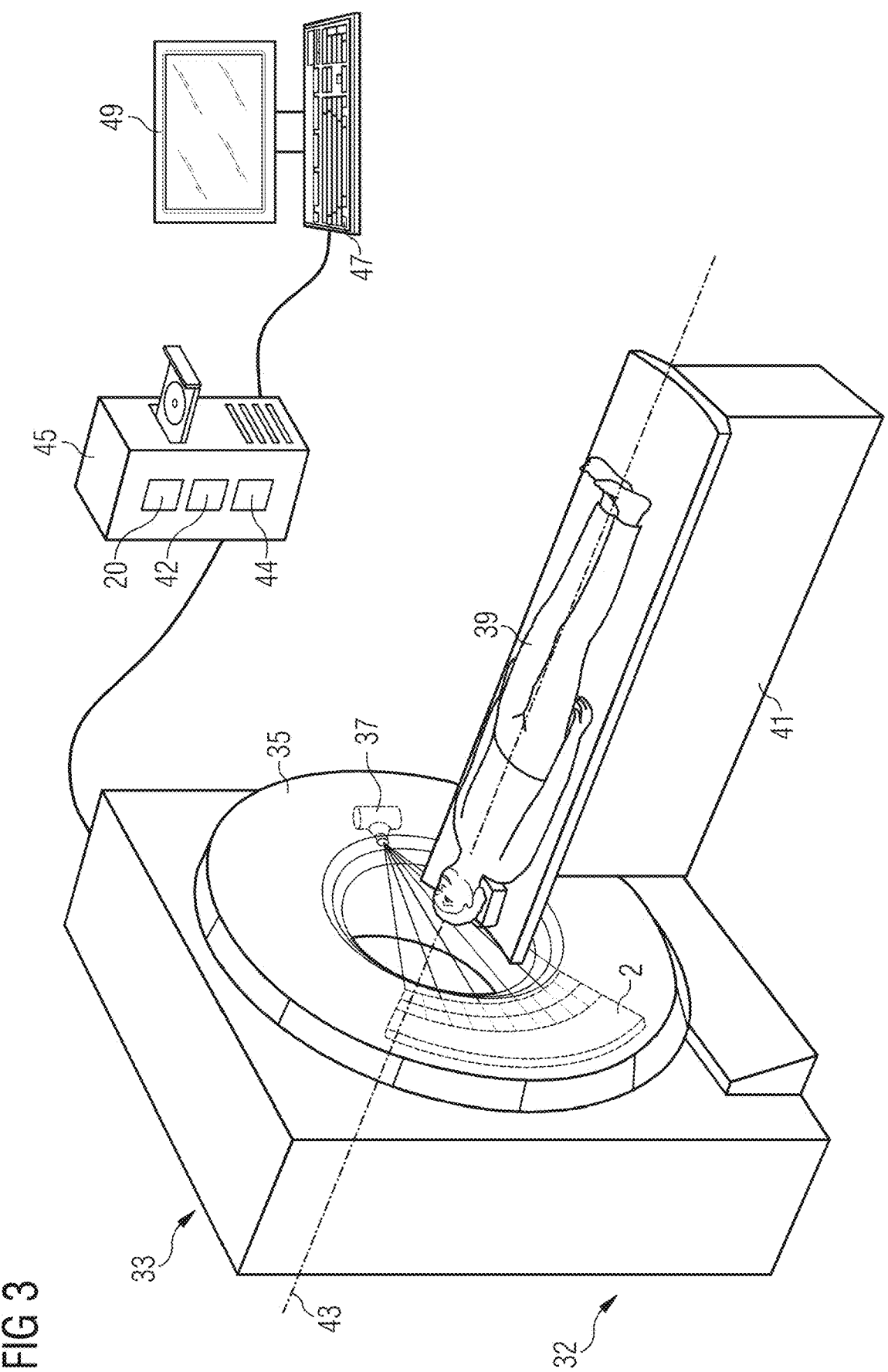
FIG. 3 is an exemplary imaging device according to an example embodiment.

FIG. 3 shows an imaging device 32 in the form of a computed tomography device.

The CT device has a gantry 33 with a rotor 35. The rotor 35 comprises at least one X-ray source 37, in particular an X-ray tube and, opposite thereto, at least one X-ray detector 2. The X-ray detector 2 and the radiation source 37 can be rotated about a common axis 43 (called the rotation axis). The patient 39 is positioned on a patient support 41 and is movable along the rotation axis 43 through the gantry 33. In general, the patient 39 can comprise, for example, an animal patient and/or a human patient.

The CT device 32 comprises a computer system 45 comprising an apparatus 20 generating a resultant image dataset. The computer system 45 further comprises a reconstruction unit 42 for reconstructing image datasets on the basis of the data established by the imaging device 32. The computer system 45 also has a control unit 44 for controlling the imaging device.

An input facility 47 and an output facility 49 are also connected to the computer system 45. The input facility 47 and the output facility 49 can enable, for example, an interaction, for example a manual configuration, a confirmation or a triggering of a method step by a user. For example, computed tomography projection datasets and/or a two-dimensional image dataset or a three-dimensional image dataset can be displayed to the user on the output apparatus 49 comprising a monitor.

Typically, scan data in the form of a plurality of (raw) projection datasets of the patient 39 are recorded from a plurality of projection angles during a relative rotation movement between the radiation source and the patient, while the patient 39 is continuously or sequentially moved through the gantry 33 via the patient support 41. Subsequently, on the basis of the projection datasets, via a mathematical method, for example comprising a filtered back projection or an iterative reconstruction method, a slice image dataset can be reconstructed for each z-position along the rotation axis within an examination region.

The apparatus for generating a resultant image dataset included by the computer system 45 is designed, in particular, to carry out a method according to one or more example embodiments of the present invention for generating a resultant image dataset.

The imaging device 32 is designed, in particular, to provide a first image dataset dependent upon a first X-ray quantum energy distribution and at least one second image dataset dependent upon at least one second X-ray quantum energy distribution. For this purpose, the X-ray detector 2 can be, for example, a spectrally-separating X-ray detector and/or the imaging device can be designed for so-called kV switching. In other embodiments, the imaging device can also comprise a so-called dual source device with two source-detector systems arranged offset to one another which operate with different emission spectra.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/ or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium, storage means or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the invention has been illustrated and described in detail by way of exemplary embodiments, the invention is not restricted by the examples disclosed and other variations can be derived therefrom by a person skilled in the art without departing from the protective scope of the invention.

The invention claimed is:

1. A method for generating a resultant image dataset of a patient, the method comprising:
    capturing a first image dataset of the patient based on a first X-ray quantum energy distribution and at least one second image dataset of the patient based on at least one second X-ray quantum energy distribution;
    first establishing a first spatial distribution of at least one first material in the patient based on the first image dataset and the at least one second image dataset via a basis material decomposition;
    second establishing background image datasets based on the first image dataset and the second image dataset, the established background image datasets including a background image dataset associated with the first X-ray quantum energy distribution and a background image dataset associated with the second X-ray quantum energy distribution;
    adapting values of the established background image datasets in regions in which the established first spatial distribution indicates a presence of the at least one first material, the adapting including applying a tissue image value associated with a respective X-ray quantum energy distribution to the values of the respective background image dataset corresponding to the X-ray quantum energy distribution, the adapting including,
        applying the adapted values to at least one of the first image dataset or the second image dataset;
    after the applying, third establishing a second spatial distribution of at least one second material in the patient based on the first image dataset and the second image dataset using a material decomposition and further based on the applying; and
    generating a resultant image dataset based on at least the second spatial distribution of the second material.

2. The method of claim 1, wherein the first establishing includes,
    subtracting the tissue image value corresponding to the X-ray quantum energy distribution from the at least one of the first image dataset or the at least one second image dataset.

3. The method of claim 2, wherein the applying includes,
    subtracting the respective adapted background image dataset corresponding to the X-ray quantum energy distribution from the at least one of the first image dataset or the at least one second image dataset.

4. The method of claim 3, wherein the at least one first material comprises calcium and the at least one second material comprises a contrast medium, and the first establishing and the third establishment includes a basis material decomposition of the at least one first material and the at least one second material, respectively.

5. The method of claim 4, wherein the second establishing includes a basis material decomposition of water and the at least one second material.

6. The method of claim 5, wherein the adapting includes,
    replacing the values with the tissue image value corresponding to the X-ray quantum energy distribution or combining the values with the tissue image value in a weighted manner.

7. The method of claim 6, further comprising:
    registering the first image dataset onto the second image dataset before the first establishing.

8. The method of claim 1, wherein the applying includes,
    subtracting the respective adapted background image dataset corresponding to the X-ray quantum energy distribution from the at least one of the first image dataset or the at least one second image dataset.

9. The method of claim 1, wherein the at least one first material comprises calcium and the at least one second material comprises a contrast medium, and the first establishing and the third establishing includes a basis material decomposition of the at least one first material and the at least one second material, respectively.

10. The method of claim 1, wherein the second establishing includes a basis material decomposition of water and the at least one second material.

11. The method of claim 1, wherein the adapting includes,
    replacing the values with the tissue image value corresponding to the X-ray quantum energy distribution or combining the values with the tissue image value in a weighted manner.

12. The method of claim 1, further comprising:
    registering the first image dataset onto the second image dataset before the first establishing.

13. The method of claim 1, further comprising:
removing noise from (i) the first image dataset and the at least one second image dataset or (ii) the resultant image dataset before the first establishing.

14. The method of claim 1, wherein the third establishing includes,
establishing a further spatial distribution of the at least one first material, wherein the generating generates the resultant image dataset based on the established second spatial distribution of the second material and the established further spatial distribution.

15. The method of claim 1, wherein the respective tissue image value comprises an image value of blood or organ tissue.

16. The method of claim 1, wherein the respective tissue image value is selectable based on an imaging application or a medical problem.

17. A non-transitory computer program product having a computer program which can be directly loaded into a memory store of an apparatus configured to generate a resultant image dataset having program portions that, when executed by the apparatus, cause the apparatus to perform the method of claim 1.

18. A non-transitory computer-readable storage medium having program portions that, when executed by an apparatus configured to generate a resultant image dataset, cause the apparatus to perform the method of claim 1.

19. An apparatus for generating a resultant image dataset of a patient, the apparatus comprising:
a first interface configured to capture a first image dataset of the patient dependent upon a first X-ray quantum energy distribution and at least one second image dataset of the patient dependent upon at least one second X-ray quantum energy distribution;
a computation unit configured to
first establish a first spatial distribution of at least one first material in the patient based on the first image dataset and the second image dataset via a basis material decomposition,
second establish background image datasets based on the first image dataset and the second image dataset, the established background image datasets including a background image dataset associated with the first X-ray quantum energy distribution and a background image dataset associated with the second X-ray quantum energy distribution,
adapt values of the established background image datasets in regions in which the established first spatial distribution indicates a presence of the at least one first material, wherein a tissue image value associated with one respective X-ray quantum energy distribution is applied to the values of the respective background image dataset corresponding to the X-ray quantum energy distribution,
third establish a second spatial distribution of at least one second material in the patient based on the first image dataset and the second image dataset using a material decomposition and further based on the adapted values, and
generate a resultant image dataset based on at least the second spatial distribution of the at least one second material; and
a second interface configured to output the resultant image dataset.

20. An imaging device comprising:
the apparatus of claim 19; and
at least one X-ray source arranged opposite to at least one X-ray detector, wherein a patient can be arranged between the X-ray source and the X-ray detector, the at least one X-ray source configured to provide the first image dataset and the at least one second image dataset.

* * * * *